United States Patent [19]

DeLuca

[11] 4,396,557
[45] Aug. 2, 1983

[54] EVAPORATIVE DISPENSER

[75] Inventor: Raymond F. DeLuca, Stamford, Conn.

[73] Assignee: Georgia-Pacific Corporation, Portland, Oreg.

[21] Appl. No.: 260,766

[22] Filed: May 5, 1981

Related U.S. Application Data

[63] Continuation of Ser. No. 65,848, Aug. 13, 1979, abandoned, which is a continuation-in-part of Ser. No. 952,386, Oct. 18, 1978, Pat. No. 4,294,778.

[51] Int. Cl.³ .............................................. A61L 9/04
[52] U.S. Cl. ............................ 261/30; 261/DIG. 65; 239/39; 422/124
[58] Field of Search .......... 261/30, DIG. 3, DIG. 65; 422/4, 5, 124, 123, 125, 305, 306; 62/314; 239/39, 40

[56] References Cited

U.S. PATENT DOCUMENTS

| 498,146 | 5/1893 | Woolley | 239/39 |
|---|---|---|---|
| 1,254,337 | 1/1918 | Marsh | 422/124 |
| 1,439,319 | 12/1922 | Mills | 422/124 |
| 1,846,068 | 2/1932 | Sandehn | 239/39 |
| 2,202,235 | 5/1940 | Smith | 261/30 |
| 4,166,087 | 8/1979 | Cline et al. | 422/124 |

FOREIGN PATENT DOCUMENTS 2227877 6/1970 France ................................ 21/124

Primary Examiner—Tim R. Miles
Attorney, Agent, or Firm—Schuyler, Banner, Birch, McKie & Beckett

[57] ABSTRACT

An evaporative dispenser is disclosed for emitting a vaporized material into the ambient. A battery powered, motor-driven fan forces air through the dispenser housing and across a material reservoir to evaporate and entrain material therein prior to being discharged from the housing. A supply container is supported directly on a reservoir lid and comprises structure which cooperates with the housing to direct the air flow across the reservoir. The supply container also comprises a battery nesting recess which affords compact packaging of the components within the housing. A transparent viewing window is provided for easy viewing of the level of material in the reservoir.

2 Claims, 31 Drawing Figures

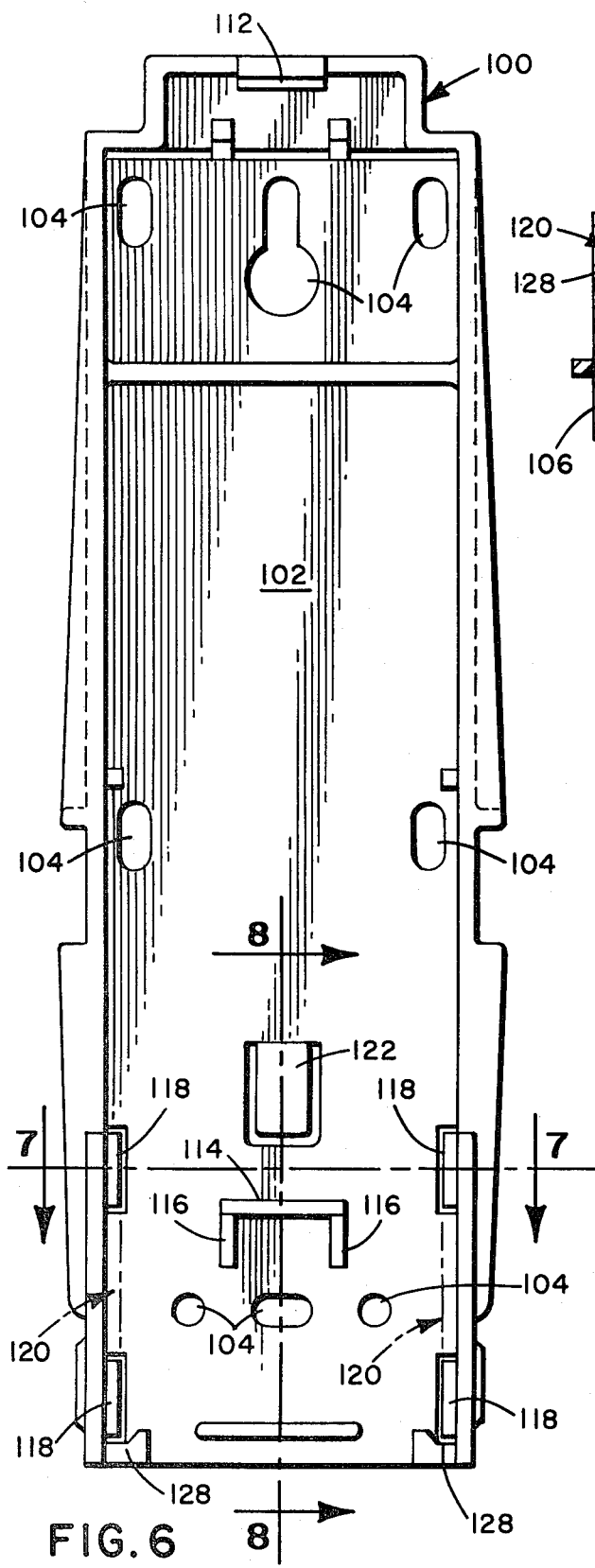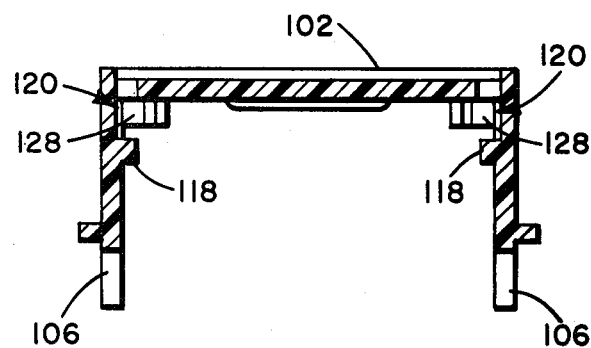
FIG. 7
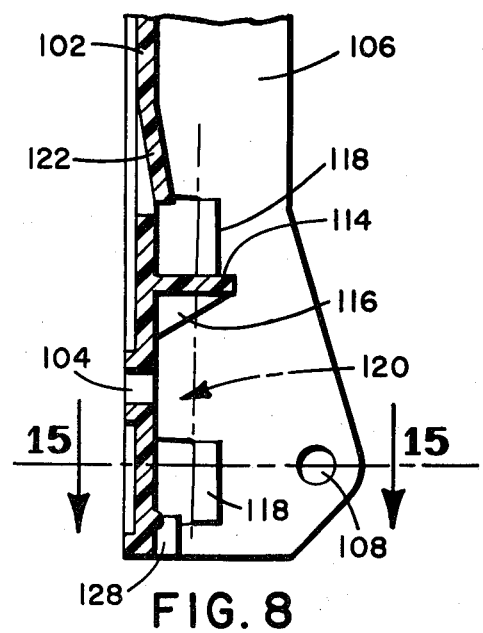
FIG. 8
FIG. 6

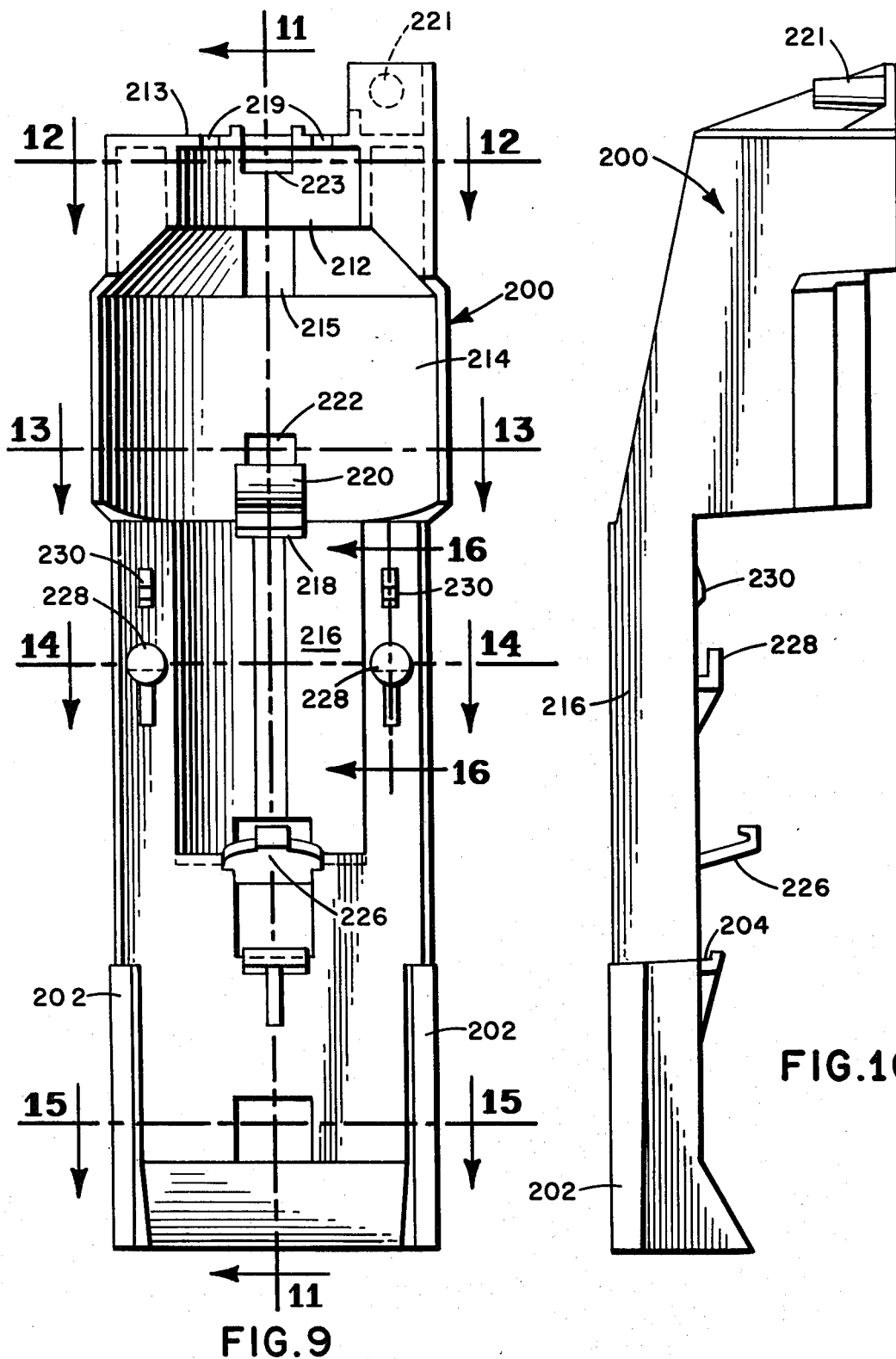

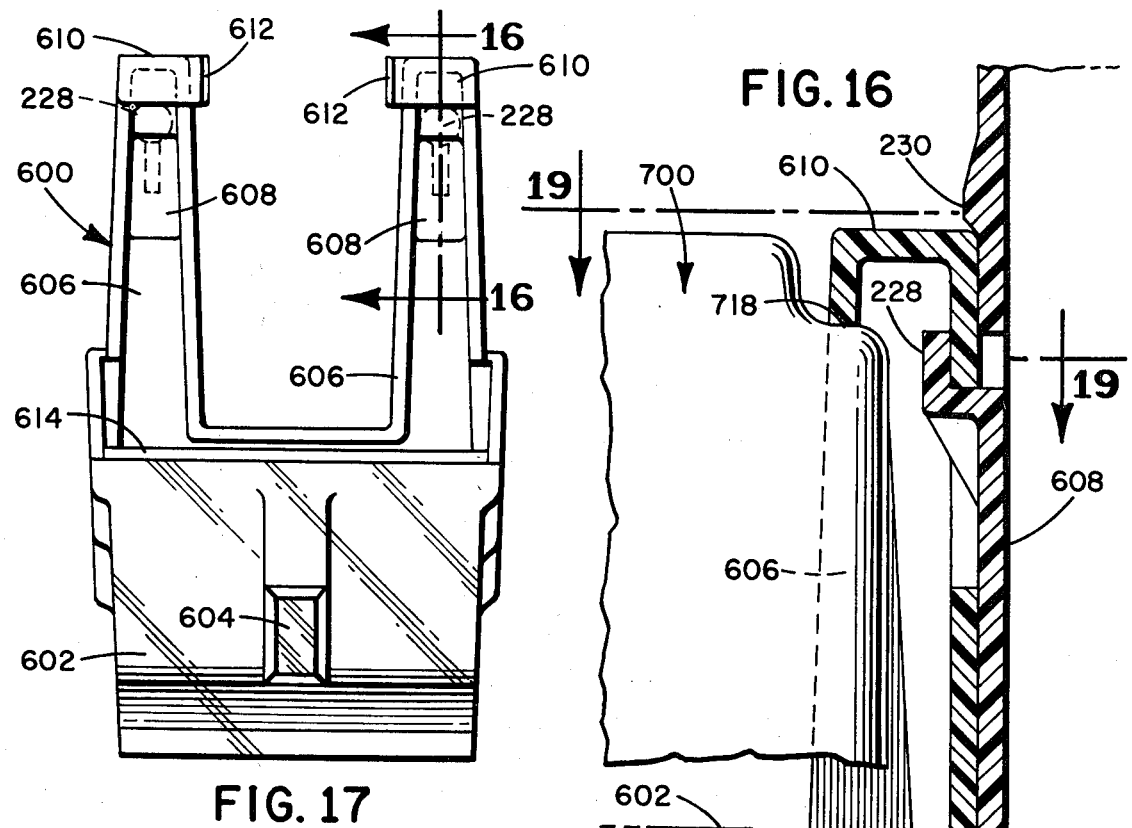
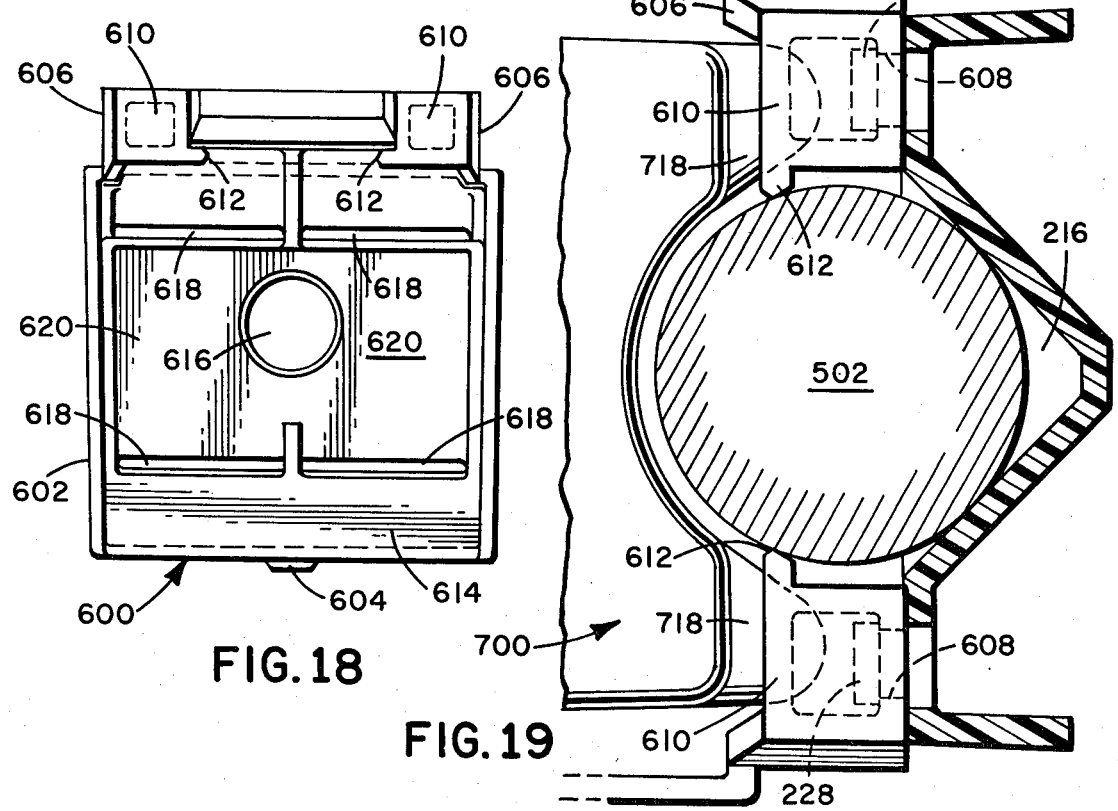

EVAPORATIVE DISPENSER

This application is a continuation of copending application Ser. No. 65,848, filed Aug. 13, 1979, now abandoned, which is a continuation-in-part of application Ser. No. 952,386, filed Oct. 18, 1978, now U.S. Pat. No. 4,294,778.

BACKGROUND OF THE INVENTION

1. Field of the Invention

The present invention relates generally to the field of dispensing a vaporized material into the ambient and, more particularly, to air freshener devices for emitting a vaporized air freshening material into the ambient.

2. Description of the Prior Art

Prior art air freshener devices are of many different types. These may be classified into two broad categories, namely, those which rely upon natural convection of room air to evaporate and diffuse air freshening material throughout a room, and those which rely upon forced air circulation (for example, by means of a motor-driven fan) to enhance the evaporative and distributive processes. Air freshener devices which fall within each of these two categories may dispense evaporated material from any one of a number of different types of sources. These include liquid-containing reservoirs, paste or gel containers and impregnated, porous media.

Some air freshener devices of the type which employs a motor-driven fan to evaporate and dispense material from an impregnated medium incorporate a cartridge-type medium which has a dry cell battery nested concentrically within the cartridge. These devices suffer the disadvantage that when either the cartridge or the battery requires replacement, both must be removed and disassembled. Impregnated media devices and gel or paste devices also suffer the disadvantage that the quantity of air freshening material remaining therein is difficult to ascertain. This is especially true in the case of impregnated media devices where it is impossible to visually observe of the amount of material remaining in the media. With devices of these types, the material supply will often be depleted and the device will operate ineffectively for a period of time until the depletion is discovered and the supply renewed. Alternatively, the supply is often renewed prior to depletion, thereby resulting in material waste.

Liquid reservoir air freshener devices have been designed which overcome this disadvantage of the other two types of air freshener devices. These liquid reservoir devices often include a material supply container or bottle for automatically replenishing the material evaporated from the reservoir. The supply bottle is typically supported in an inverted position above the reservoir with the open mouth of the bottle in contact with the surface of the liquid in the reservoir. With such an arrangement, liquid material will flow out of the supply bottle only when the liquid level within the reservoir drops below the mouth of the bottle to break the suction and permit air to enter the bottle. An absorbent wick is often placed partially inside the reservoir to enhance the evaporative process.

In air freshener devices of this type, the supply bottle can be replaced when empty without interrupting the air freshening function of the device because a quantity of liquid material still remains within the reservoir for evaporation into the ambient. However, prior art devices of this type have no provision for ascertaining the level of liquid within the reservoir without dismantling at least a portion of the device itself. Hence, substantial effort is required to monitor the condition of the reservoir and supply bottle of these prior art devices. Often, the supply bottle may be emptied and the material completely evaporated from the reservoir before the depleted condition is discovered. In addition, complex supporting structures are often used in these prior art devices for supporting the supply bottle above the reservoir.

Prior art air freshener devices which function as liquid evaporators by employing motor-driven fans typically are not compact in construction. The deodorant material supply, battery and motor-driven fan are often mounted at spaced locations within a boxy or cumbersome housing, with little attention given to efficient packaging. These devices make use of a wick structure immersed in a reservoir containing a quantity of liquid material to be dispensed into the ambient. Substantially all of the vaporization of this material occurs from the surface of the wick itself, and the liquid supply is replenished only infrequently. These devices suffer the disadvantage that the amount of deodorizer that is vaporized gradually diminishes as the supply in the reservoir decreases. This results in an excessive release of fragrance at the start, and an insufficient release towards the end. This is due to the dilution of the concentration of the volatile fragrances as time passes, since the reservoir is always open, and the crusting over of the vaporization surfaces with the passage of time.

The prior art is, therefore, devoid of a wall-mounted air freshener device which is efficient, reliable, compact, attractive and unobtrusive.

SUMMARY OF THE INVENTION

Accordingly, it is an object of the present invention to obviate the above noted disadvantages of the prior art by providing an evaporative dispenser which is attractive in appearance, compact in construction and efficient in operation.

Another object of the present invention is to provide an evaporative dispenser and method for emitting vaporized material into the ambient at a controlled, substantially uniform rate.

Another object of the invention is to provide an evaporative dispenser and method for emitting vaporized material into the ambient wherein the vaporization surfaces are automatically and frequently renewed to prevent encrustation thereof.

Another object of the present invention is to provide an evaporative dispenser which utilizes a material supply bottle having contours which form part of the operating structure of the dispenser by channelling air across a material reservoir.

Another object of the present invention to provide an evaporative dispenser having a simple supporting structure for a material supply container.

Another object of the present invention is to provide an evaporative dispenser having means for retaining a material supply bottle in position within the dispenser.

Another object of the present invention is to provide an evaporative dispenser having a battery-powered, motor-driven fan and a material supply container wherein the battery is compactly nested against the container and the container is readily removable for replacement without the necessity of removing the battery.

Another object of the present invention is to provide an evaporative dispenser wherein a motor-driven fan, a material supply container and a material reservoir are compactly mounted in relation to one another to minimize wasted space within the dispenser.

Another object of the present invention is to provide an evaporative dispenser having a material reservoir wherein the quantity of material remaining in the reservoir can be readily ascertained from the outside of the dispenser without having to dismantle any portion thereof.

Another object of the present invention is to provide a material supply container having structure which adapts it for use with the evaporative dispenser of the invention.

Another object of the present invention is to provide a contoured dispensing container which can be compactly nested for storage with other containers of the same type.

These and other objects of the present invention are accomplished by means of a method of emitting a vaporized material into the ambient at a controlled, substantially uniform rate from a substantially open reservoir containing an exposed liquid quantity of the material, comprising the steps of producing and directing a forced flow of air past and close to the surface of the liquid in the reservoir to effect vaporization of the liquid from the surface thereof and directly entrain the vaporized material therein, and continually and automatically replenishing material evaporated from the reservoir by discharging fresh liquid directly onto the surface of the liquid in the reservoir to renew the surface and prevent stagnation thereof. The invention also encompasses an evaporative dispenser for carrying out the above method steps.

A motor-driven fan, the material supply bottle and the material reservoir are all compactly stacked within the dispenser housing. The fan establishes an entraining flow of air through the housing and across the reservoir. The interior structure of the housing need not contain air channelling baffles because the material supply container is contoured to fit within a container-receiving cavity and cooperate with the housing to direct air flowing through the housing across the reservoir. A simple supporting and retaining arrangement enables the supply container to be directly supported and retained by the reservoir. The supply container is formed with a recess in which a battery nests when the supply container is in position within the cavity. The battery is retained in a separate support and need not be removed when the supply container is to be replaced. A viewing window formed in the housing is located in registry with a transparent portion of the reservoir so that the level of material within the reservoir can be ascertained without opening the housing.

The invention also encompasses a container which is adapted for use with the evaporative dispenser of the invention. The container has a protrusion formed opposite the battery recess, the protrusion cooperating with the housing wall to define an airway for directing air towards the reservoir. A sloped wall of the supply container accelerates and channels the air across the reservoir. The battery recess in the container is larger than the protrusion so that several containers can be compactly nested for storage, with the protrusion of one container nesting within the recess of an adjacent container.

BRIEF DESCRIPTION OF THE DRAWINGS

The novel features of the invention are set out with particularity in the appended claims, but the invention will be understood more fully and clearly from the following detailed description of a preferred embodiment of the invention as set forth in the the accompanying drawings, in which:

FIG. 6 is a front elevational view of the backplate of the dispenser;

FIG. 7 is a horizontal sectional view of the same taken along 7—7 of FIG. 6;

FIG. 8 is a partial vertical sectional view of the same taken along line 8—8 of FIG. 6;

FIG. 9 is a front elevational view of the chassis of the dispenser;

FIG. 10 is a side elevational view of the same;

FIG. 16 is a partial vertical sectional view of the assembled chassis and reservoir support taken along line 16—16 of FIGS. 9 and 17, and showing the relative position of the supply container;

FIG. 17 is a front elevational view of the reservoir assembly of the dispenser;

FIG. 18 is a plan view of the same;

FIG. 19 is a horizontal sectional view of the chassis taken along line 19—19 of FIG. 16, and showing the relative positions of battery, reservoir support and supply container;

DESCRIPTION OF PREFERRED EMBODIMENTS

Figure 1:
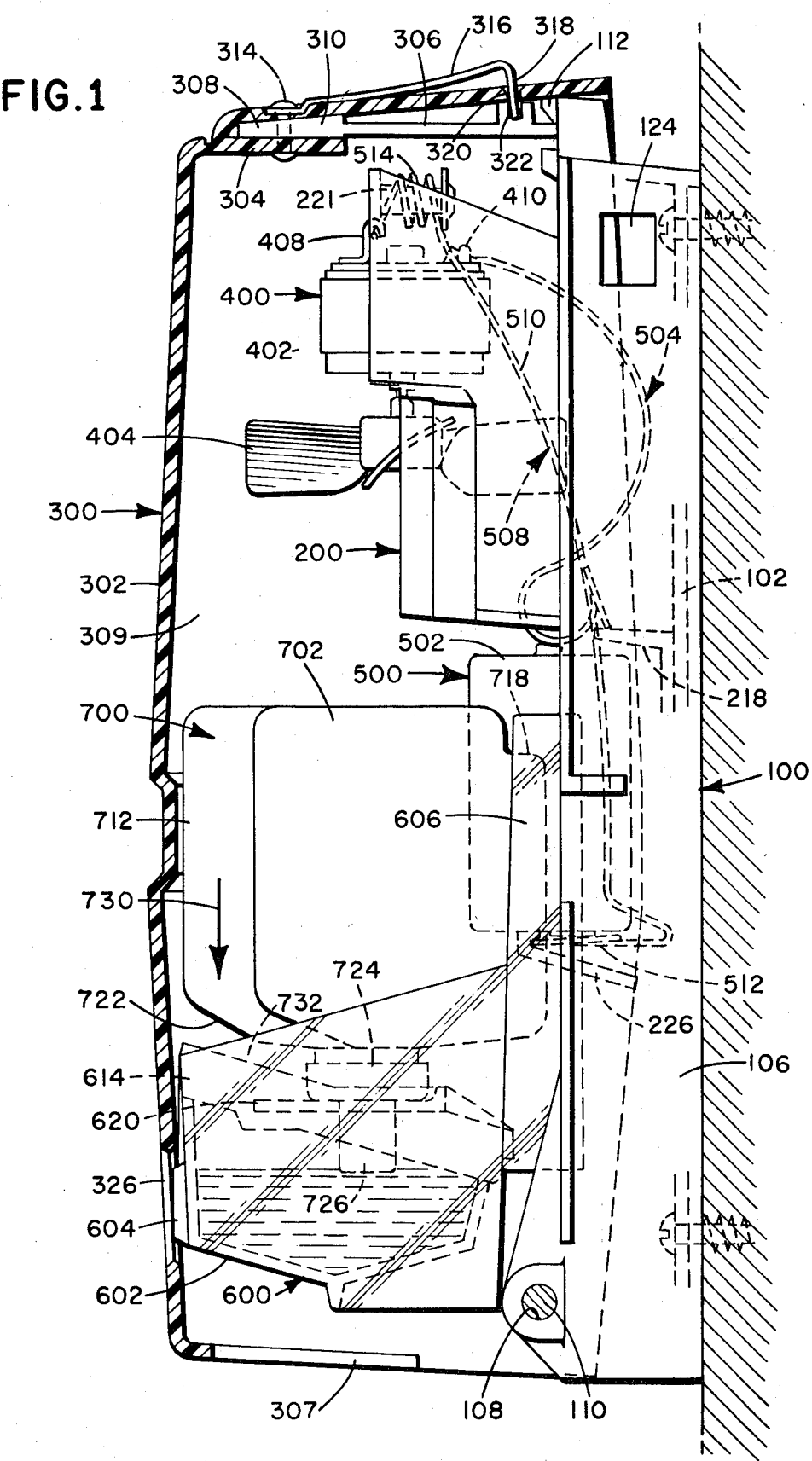
FIG. 1 is a side elevational view of the dispenser with the housing shown in section.
Figure 2:
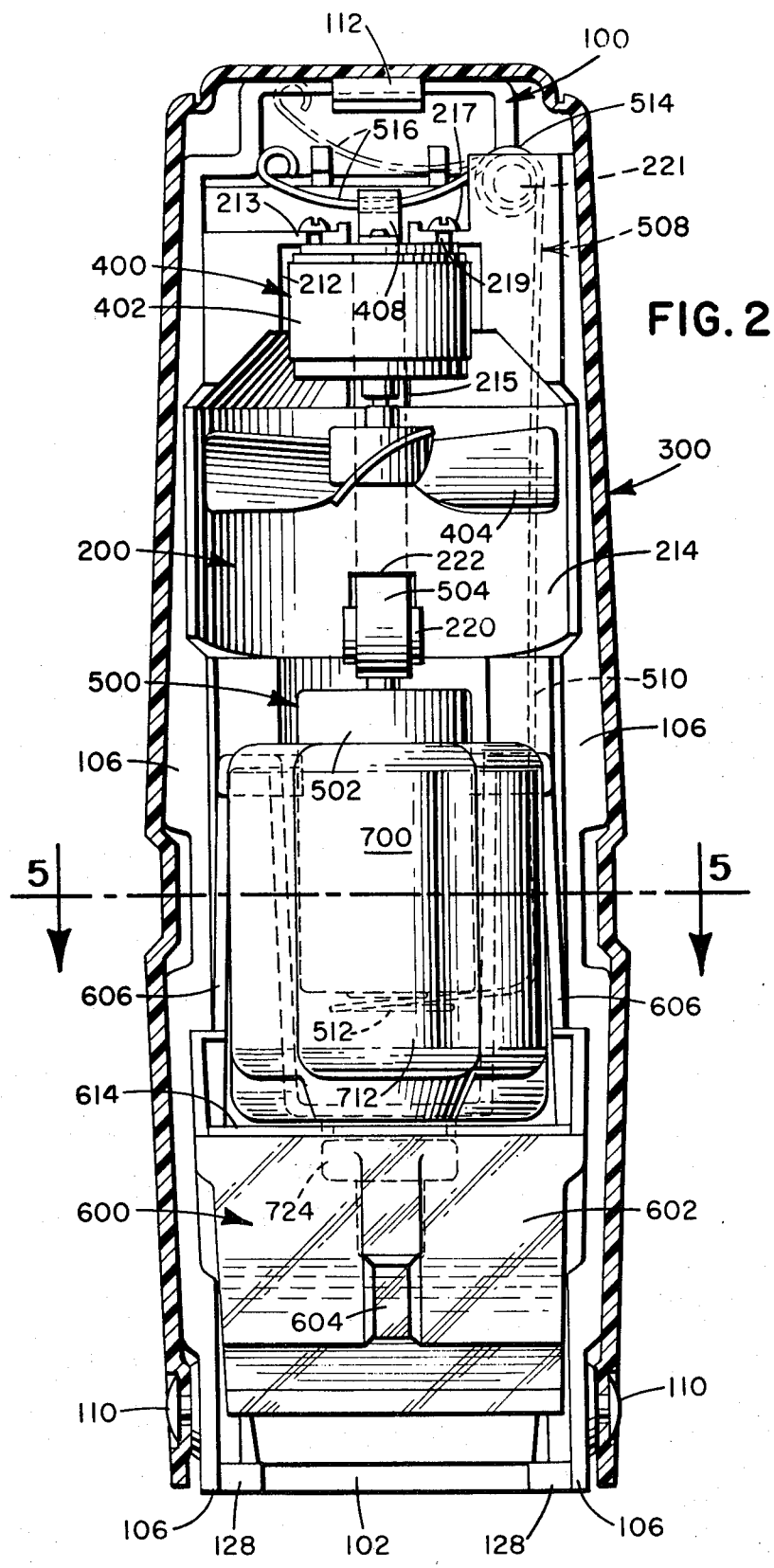
FIG. 2 is a front elevational view of the dispenser with the housing shown in section.
Figure 3:
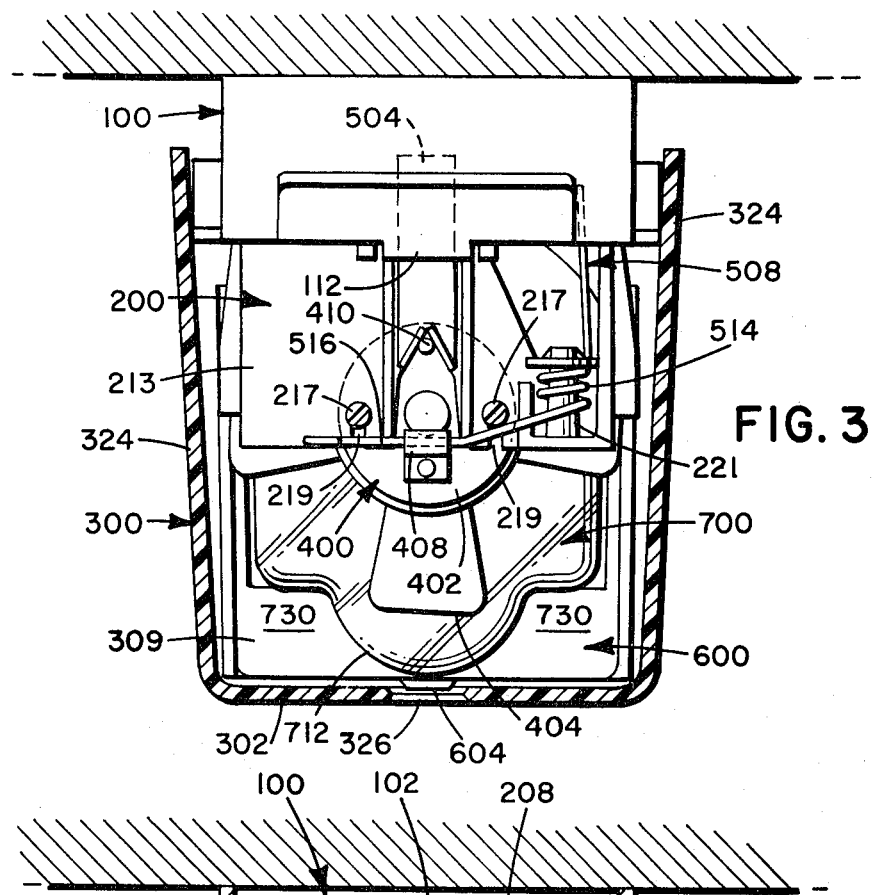
FIG. 3 is a plan view of the dispenser with the housing shown in section.
Figure 5:
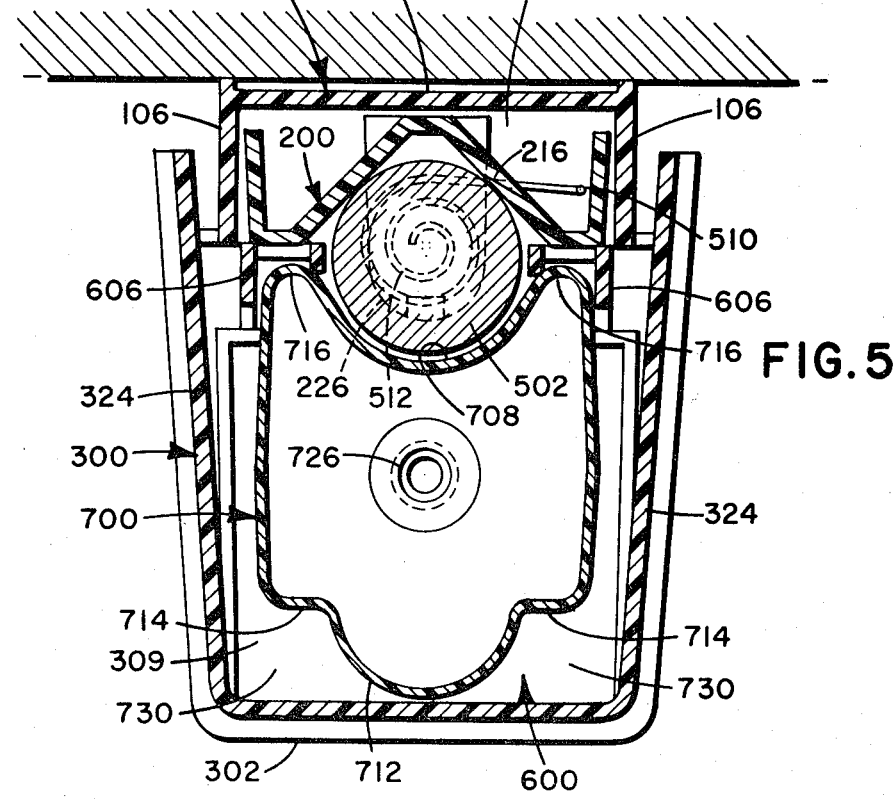
FIG. 5 is a horizontal sectional view of the dispenser taken along line 5—5 of FIG. 2.
Figure 4:
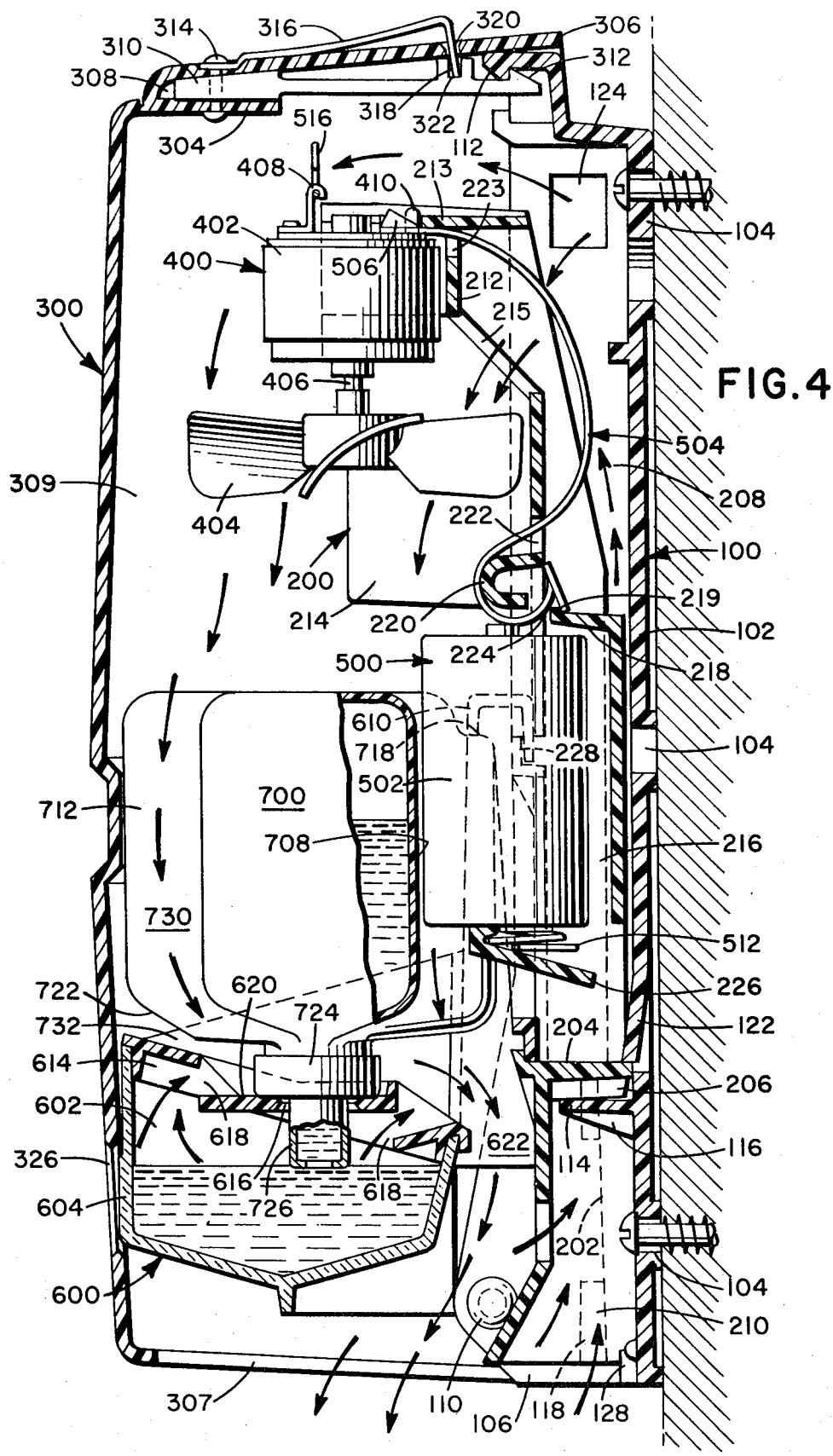
FIG. 4 is a vertical sectional view of the dispenser.
Figure 11:
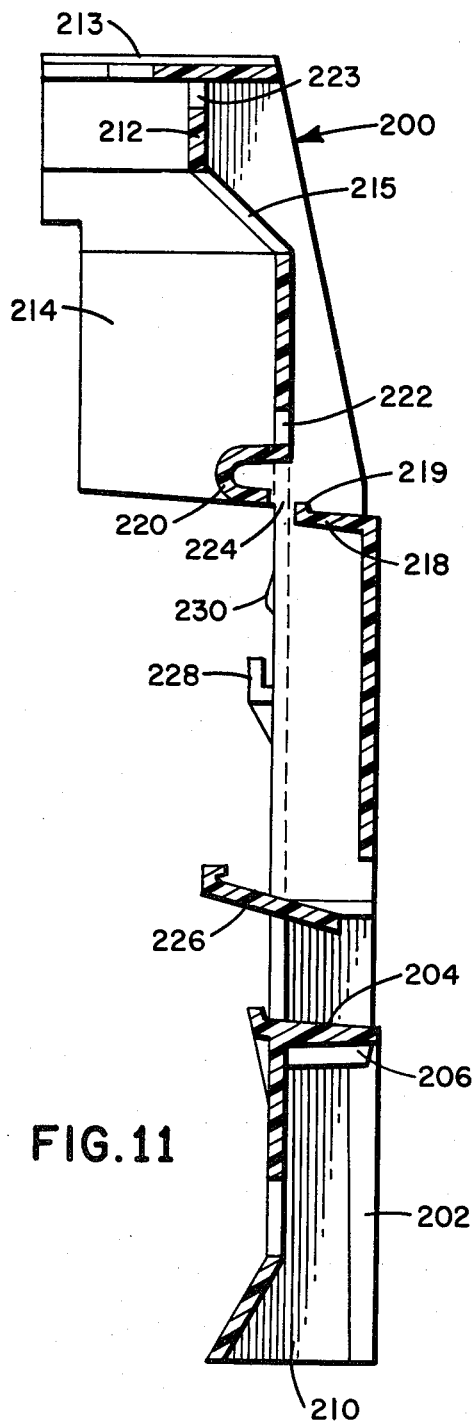
FIG. 11 is a vertical sectional view of the same taken along line 11—11 of FIG. 9.
Figure 12:
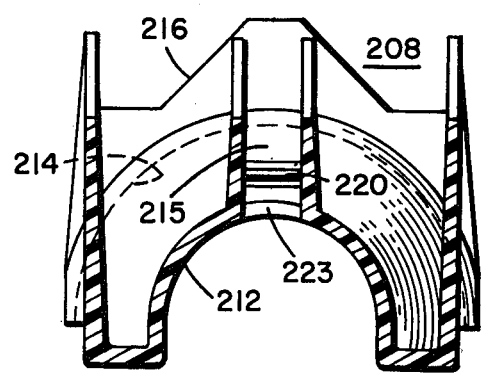
FIG. 12 is a horizontal sectional view of the same taken along line 12—12 of FIG. 9.
Figure 13:
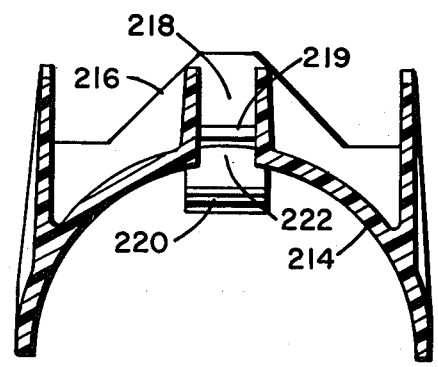
FIG. 13 is a horizontal sectional view of the same taken along 13—13 of FIG. 9.
Figure 14:
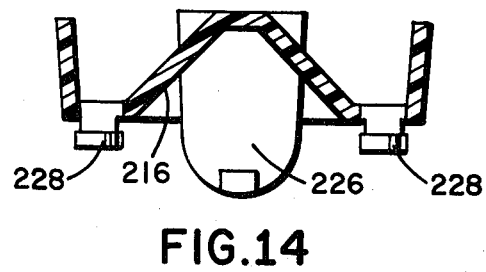
FIG. 14 is a horizontal sectional view of the same taken along line 14—14 of FIG. 9.

The dispenser of the present invention may taken the form of an air freshener device which is adapted for wall mounting in restrooms or the like. The exterior appearance of this air freshener is substantially identical to that of the liquid soap dispenser disclosed in U.S. Pat. No. 4,036,406, and is intended for companion use therewith. The air freshener comprises seven subassemblies designated by the following series of reference numerals:

- 100 backplate
- 200 chassis
- 300 housing
- 400 motor and fan assembly
- 500 battery and lead assembly
- 600 reservoir assembly
- 700 supply container Referring to FIGS. 1 through 5, these subassemblies are generally related as follows. Backplate 100 is adapted to be mounted to a wall and supports chassis 200 and housing 300. Motor and fan assembly 400, battery and lead assembly 500, and reservoir assembly 600 are all secured to chassis 200. Supply container 700 is supported on reservoir assembly 600.

BACKPLATE

Referring to FIGS. 1 through 8, backplate 100 is a molded plastic subassembly comprising a rear wall 102 having a plurality of mounting holes 104 through which mounting screws may be installed. Side flanges 106 extend forwardly from rear wall 102 and contain holes 108 through which pivot pins 110 pass for pivotally mounting housing 300 to the backplate. A protruding locking tab 112 extends forwardly from rear wall 102 for engaging the upper portion of housing 300.

A protruding seat 114 extends forwardly from rear wall 102 and is reinforced by webs 116. Guides 118 extend inwardly from side flanges 106 to define tapered, sub-vertical channels 120 bounded in the rear by rear wall 102, on the sides by side flanges 106, at the front by guides 118 and at the bottom by inwardly extending stops 128. Channels 120 slidably receive and support mating structure of chassis 200, as explained more fully below. The taper of channel 120 provides a wedging action between the chassis structure and the backplate. A slanted tab 122 protrudes between channels 120 and is deflected rearwardly by the insertion of the chassis, and then snaps forwardly to engage a mating shoulder of the chassis when the chassis is bottomed in channels 120 against stops 128. Apertures 124 formed in side flanges 106 serve as two of several inlets for air entering the dispenser.

CHASSIS

Figure 15:
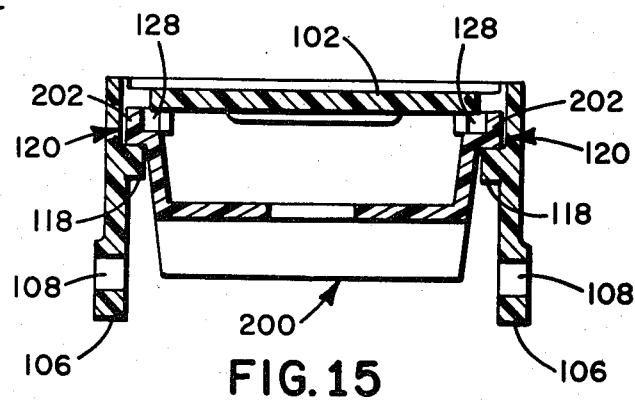
FIG. 15 is a horizontal sectional view of the assembled backplate and chassis taken along line 15—15 of FIGS. 8 and 9.

Referring to FIGS. 1 through 5 and 9 through 15, chassis 200 is also a molded plastic subassembly and comprises a generally vertically extending, contoured structure having a pair of tapered, laterally extending mounting rails 202 formed near the bottom thereof. A rearwardly extending tab 204 is provided with a bottom reinforcing flange 206. Chassis 200 is supported on backplate 100 by inserting the lower ends of mounting rails 202 into channels 120 behind upper tabs 118 and pressing the chassis downwardly until it bottoms against stops 128, as illustrated in FIG. 15. At this point, flange 206 is firmly seated against seat 114, and tab 122, having been deflected rearwardly by tab 204, snaps forwardly to firmly engage the upper surface of tab 204 (see FIG. 4). The chassis is thus firmly wedged and locked in place on the backplate and is supported over approximately the bottom one-quarter of its height. A longitudinal channel 208 is formed between chassis 200 and backplate 100. This channel, with its open bottom 210, serves as an additional air inlet. Air is drawn upwardly through channel 208 to the space above the motor and fan assembly.

An upper arcuate recess 212 cradles the motor of the fan and motor assembly 400. The motor is secured to horizontal flange 213 by means of screws 217 which extend through slots 219 formed in flange 213. A flange-mounted post 221 provides support for one end of one of the spring leads connected to the motor. A lower, larger arcuate recess 214 defines a partial shroud for the fan. An aperture 215 formed between arcuate recesses 212 and 214 communicates with air channel 208 and air inlet apertures 124.

A generally V-shaped battery tray 216 is formed below recess 214. Battery tray 216 comprises an upper flange 218 having a lip 219 which, in cooperation with nose portion 220 and apertures 222 and 224, accommodates the end of one of the spring leads which electrically connect the battery to the motor. The other end of this lead is trained through aperture 223. Battery tray 216 further comprises a lower hooked shelf 226 which supports the end of the other spring lead.

Forwardly extending hooks 228 cooperate with protrusions 230 to support and lock a hanging arm of reservoir assembly 600 (see FIG. 16). An additional lower shelf 232 provides support for a lower portion of reservoir assembly 600 (see FIG. 4).

HOUSING

Referring to FIGS. 1 through 5, housing 300 comprises a front wall 302, side walls 324, a top flange 304 and a top wall 306. The bottom of the housing is substantially open to form an outlet 307 for air and entrained vaporized air freshening material. The housing walls and other internal structure define a container receiving cavity 309.

Flange 304 and wall 306 define a space 308 therebetween for the reception of a locking member 310 which has a hooked nose portion 312 adapted to engage locking tab 112. Locking member 310 is retained in position by means of a rivet 314. Rivet 314 also secures a releasing spring lever 316 to top wall 306. Spring lever 316 has a leg portion 318 which extends through a hole 320 in top wall 306 to engage a seat 322 formed on locking member 310. By manually depressing spring lever 316, locking member 310 is deflected downwardly to uncouple nose portion 312 from locking tab 112. Side walls 324 are pivoted to side flanges 106 of backplate 100 by means of pins 110 which extend through apertures 108 formed in side flanges 106. Housing 300 may therefore be unlatched at the top by manually depressing spring lever 316 and swung downwardly about pins 110 to reveal the interior of the dispenser.

A viewing window 326 is formed in the lower portion of front wall 302. This viewing window is in registry with a transparent portion of the reservoir assembly 600. This permits the material level within the reservoir to be monitored without having to dismantle any portion of the dispenser.

MOTOR AND FAN ASSEMBLY

Referring to FIGS. 1 through 5, motor and fan assembly 400 comprises a motor 402 secured to chassis 200 as described above. A multi-bladed fan 404 is secured to the shaft 406 of motor 402. The blades of fan 404 have a pitch and direction of rotation such that an air flow is established downwardly through the housing, thereby drawing air into the housing through apertures 124, and opening 210. One terminal of motor 402 comprises a hook member 408 which retains one end of one of the spring leads extending from the battery. The other motor terminal comprises a post 410 which is engaged by the bifurcated end of the other spring lead.

BATTERY AND LEAD ASSEMBLY

Referring to FIGS. 1 through 5, 19 and 21 through 23, battery and lead assembly 500 comprises a replaceable cylindrical dry cell battery 502 which is frictionally and resiliently supported in battery tray 216 of chassis 200 between the ends of two spring leads. Upper spring lead 504 comprises a flat strip of springy metal in its relaxed (uninstalled) state (see FIGS. 22 and 23) having a bifurcated tip 506 which engages motor terminal 410. The other end of spring lead 504 has a pair of prongs which engage behind lip 219 of flange 218. As described above, the spring lead is trained through aperture 224, around nose portion 220, through aperture 222 and through aperture 223 into engagement with motor terminal 410.

Figure 20:
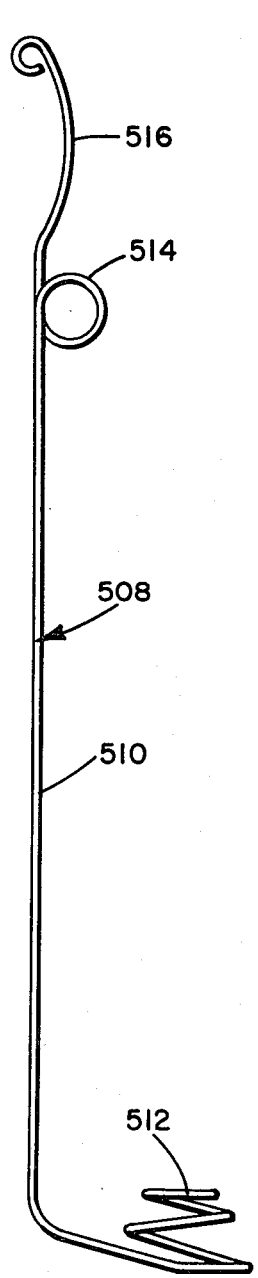
FIG. 20 is a side elevational view of one spring lead for connecting the battery to the motor, shown in its relaxed state.
Figure 21:
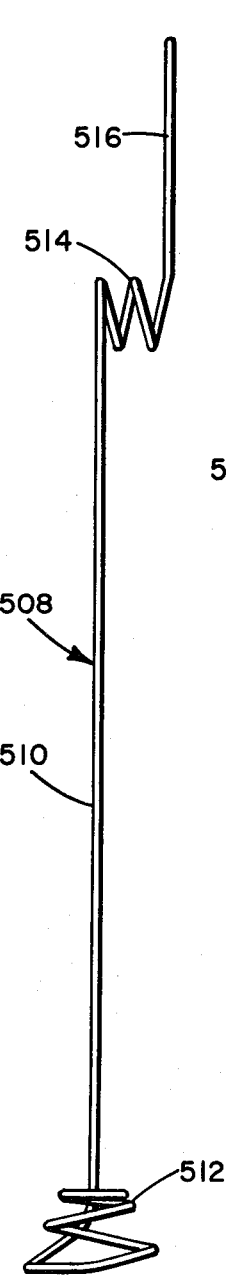
FIG. 21 is a front elevational view of the same.
Figure 22:
FIG. 22 is a front elevational view of the other spring lead for connecting the battery to the motor, shown in its relaxed state.
Figure 23:
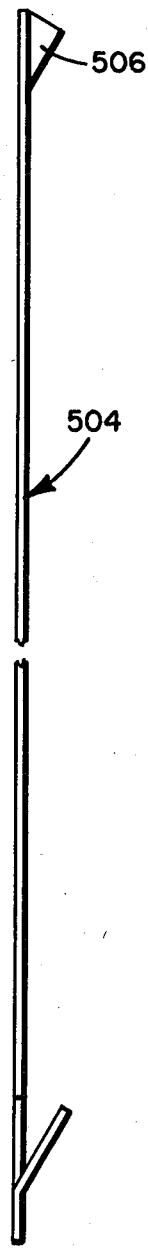
FIG. 23 is a side elevational view of the same.

The other spring lead 508 comprises a spring wire of round cross-section having a generally straight center portion 510 in its relaxed state (see FIGS. 20 and 21). The lower end of spring lead 508 comprises a spiral coil 512 which is retained in hooked shelf 226 of chassis 200. The opposite end of this spring lead comprises a helical coil 514 which is trained about post 221 of chassis 200. A tip 516 which extends laterally of helical coil 514 is biased upwardly by coil 514 but is retained by hook terminal 408. The motor may be shut off by manually depressing tip 516 and moving it laterally out of engagement with hook terminal 408.

RESERVOIR ASSEMBLY

Referring to FIGS. 1, 2, 4 and 16 through 19, reservoir assembly 600 comprises a reservoir 602 for containing a quantity of liquid odorant or deodorant material to be evaporated. Reservoir 602 may have a transparent portion 604 formed at the front thereof in registry with viewing window 326, but preferably it is made completely of transparent plastic. Upstanding arms 606 are integrally formed with reservoir 602 and serve to support the entire assembly on hooks 228 of chassis 200 by means of rearwardly facing apertures 608. Arms 606 carry lateral projections 610 near their upper ends which overlie and engage shoulders formed on the supply container. Inwardly extending tabs 612 are carried by lateral projections 610 and serve to hold battery 502 in position in its recess 216 (See FIG. 19).

Reservoir 602 supports a lid 614 having a circular central aperture 616 and a plurality of louvers or slots 618. The central flat portion 620 which surrounds aperture 616 acts as a supporting surface for the supply container. Lid 614 slopes gradually downwardly towards backplate 100, terminating ahead of chassis 200 to define a channel 622 through which air with entrained vaporized material will pass on its way to outlet 307.

Figure 27:
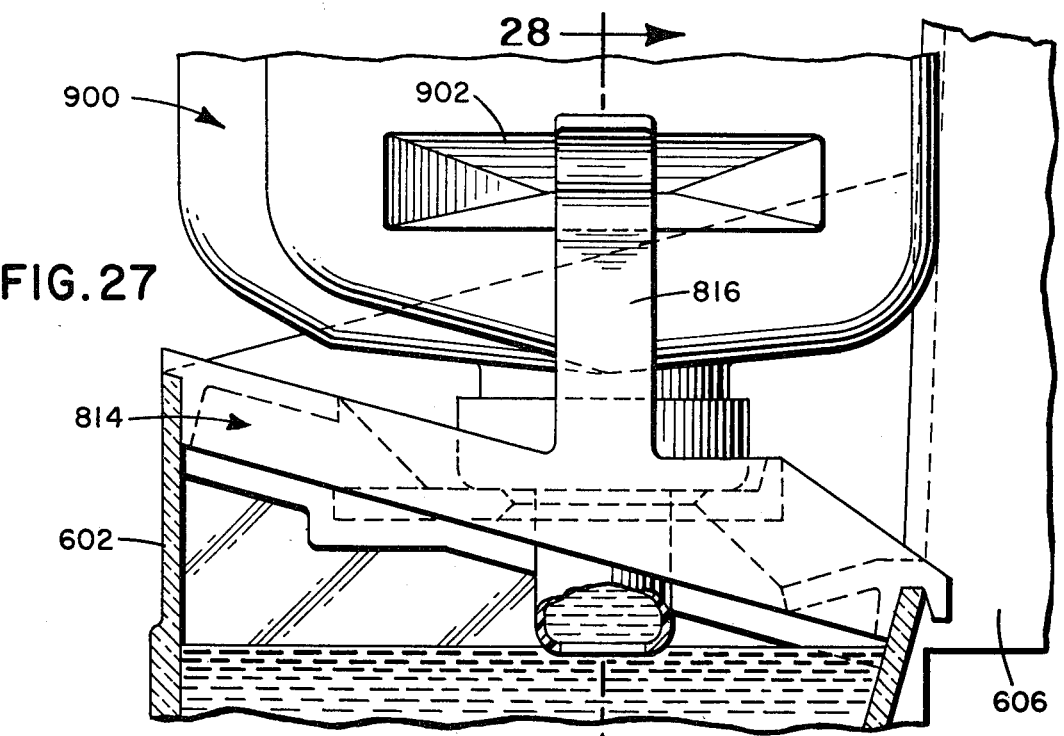
FIG. 27 is a side elevational view of an alternative embodiment of the invention.
Figure 28:
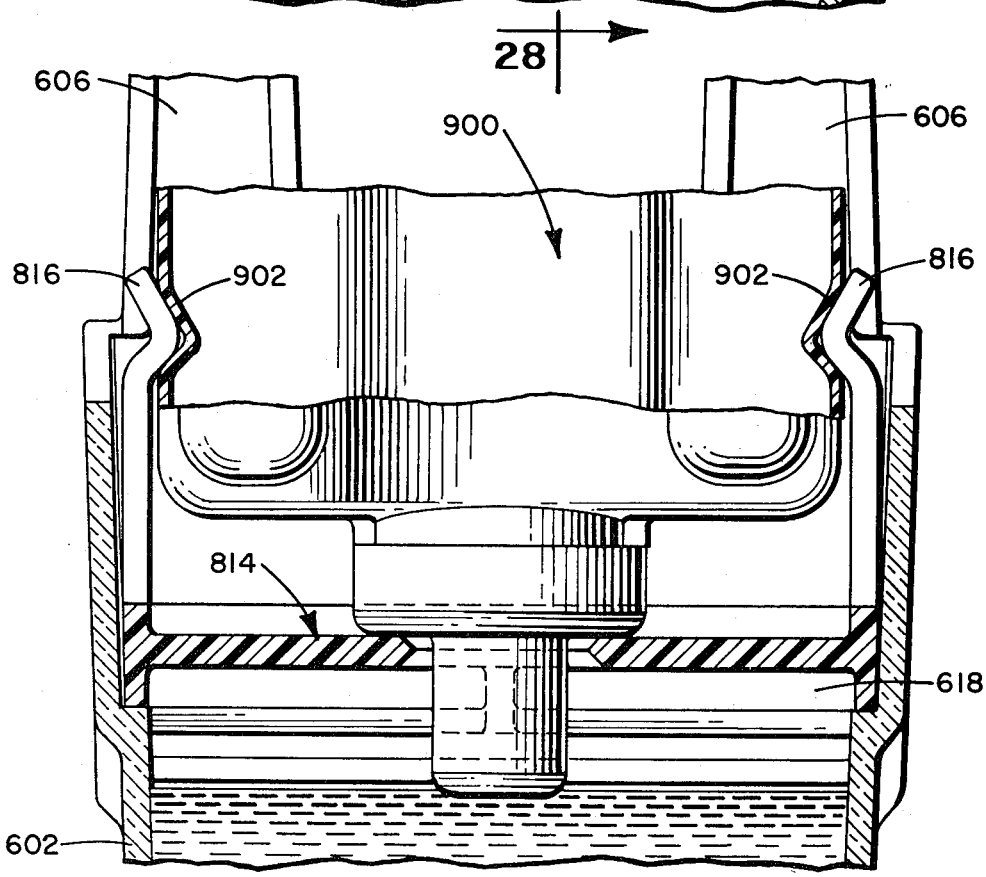
FIG. 28 is a sectional view of the same taken along line 28—28 of FIG. 27.

An alternative embodiment of lid 614 is illustrated in FIGS. 27 and 28. This lid is adapted to support the type of supply container illustrated in FIGS. 29, 30 and 31 and described below. Lid 814 is provided with an opposed pair of snap tabs 816 which cooperate with the dimples formed in container 900 to retain it in position on the lid. The resiliency of snap tabs 816 and that of the container walls both contribute to this snap-acting retention of the container.

SUPPLY BOTTLE

Figure 24:
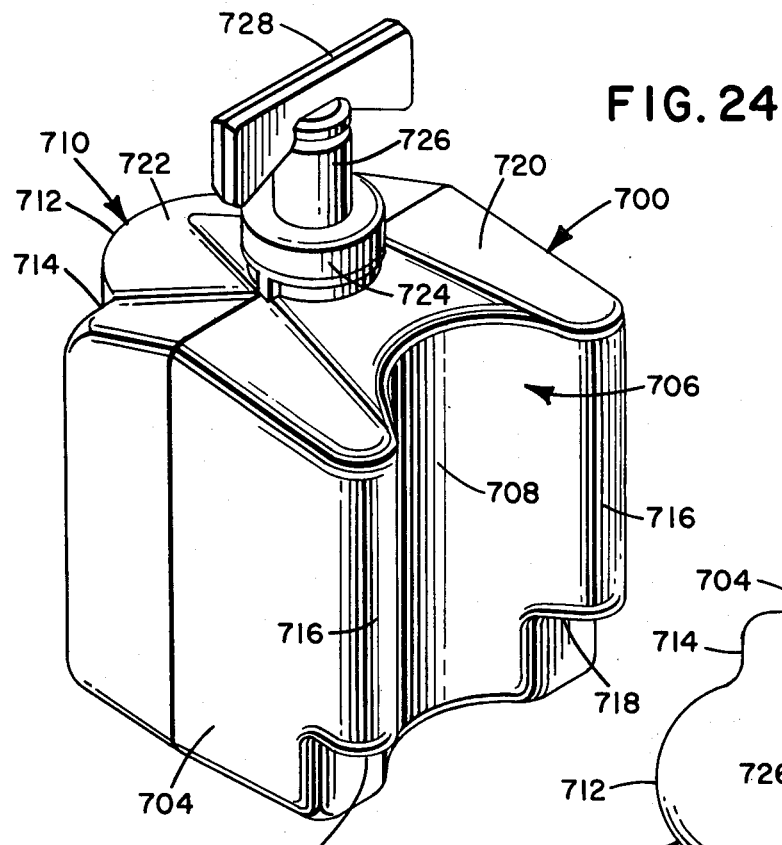
FIG. 24 is a perspective view of one embodiment of the supply container used in the dispenser.
Figure 25:
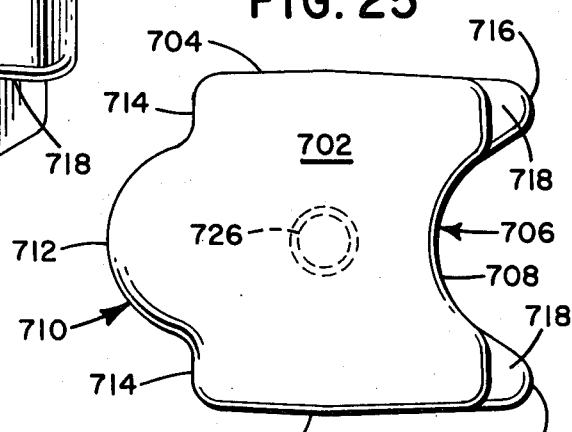
FIG. 25 is a bottom view of the same.
Figure 26:
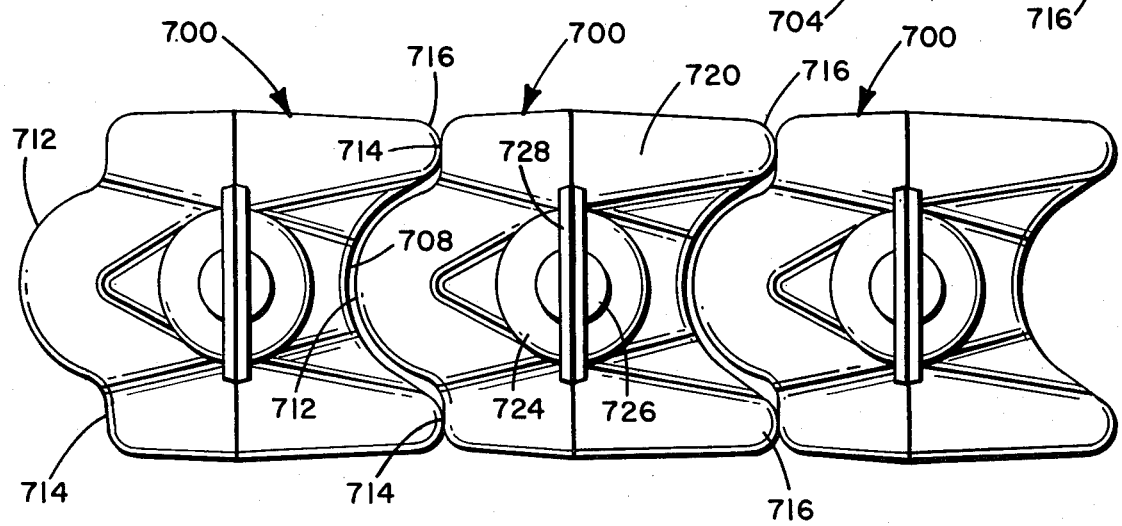
FIG. 26 shows a plurality of supply containers in nested relationship.

Referring to FIGS. 24 through 26, material supply container 700 is molded of high density polyethylene and has a bottom wall 702 joined to two pairs of opposed side walls. Side walls 704 are substantially flat and parallel, while side wall 706 comprises a central recess 708. Side wall 710, on the other hand, comprises a central protrusion 712 which is flanked by a pair of shoulders 714. Recess 708 is flanked by a pair of ridges 716 which extend less than the full height of the container to define shoulders 718. Top wall 720 comprises a sloped portion 722 adjacent protrusion 712. An annular collar 724 surrounds an outlet tube 726. A break-off closure 728 closes outlet tube 726.

This configuration of opposed recess and protrusion enables a plurality of these supply containers to be nested for compact storage as illustrated in FIG. 26. As seen in FIGS. 1 through 5 and 19, this configuration also enables supply container 700 to compactly nest around battery 502. Collar 724 functions to support container 700 in an inverted position on central flange 620 of lid 614 with outlet tube 726 extending through central aperture 616 and into fluid communication with material contained in reservoir 602. When in this position, shoulders 718 of container 700 are engaged by lateral projections 610 of arms 606 (see FIGS. 16 and 19).

Figure 29:
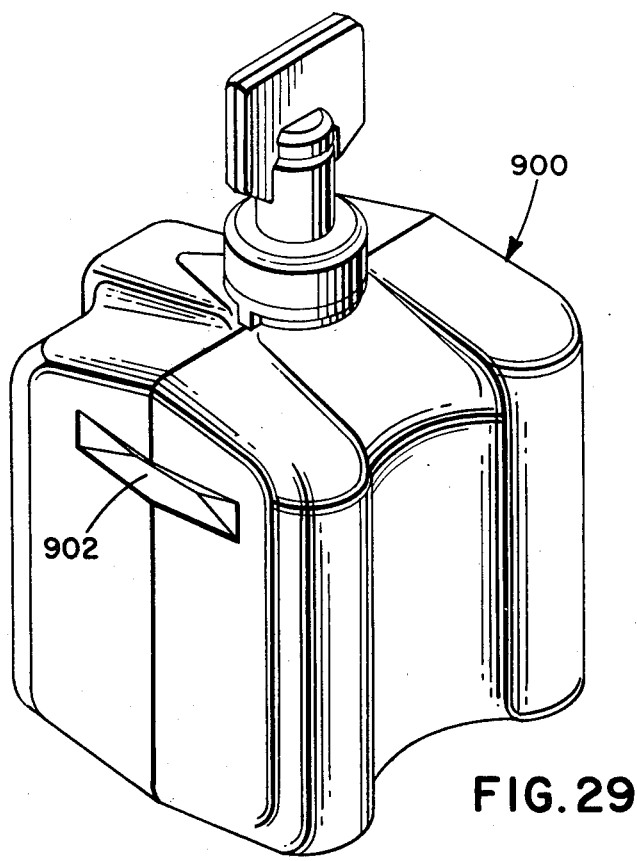
FIGS. 29 through 31 depict an alternative embodiment of the supply container of the invention.
Figure 30:
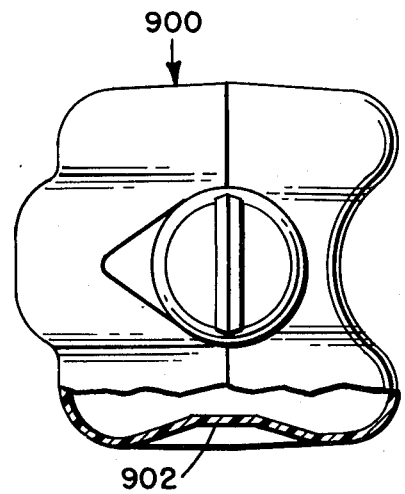
Figure 31:
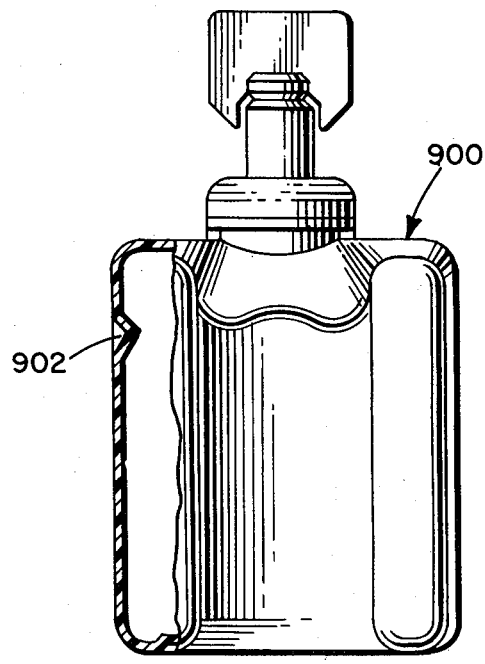

An alternative embodiment of the supply container is illustrated in FIGS. 29, 30 and 31. Container 900 is generally similar in capacity, size and shape to container 700 and is also nestable with others of the same type. However, container 900 is devoid of shoulders 718 because an alternative container engaging means in the form of two opposed dimples 902 are formed in the container wall. Dimples 902 are engaged by snap tabs 816 of lid 814, which firmly retain container 900 in position, as seen in FIGS. 27 and 28. Container 900 also is slightly thinner than container 700 so as to clear retaining projections 610. Of course, projections 610 serve no functional purpose when container 900 is used.

OPERATION

Reservoir lid 614 defines a substantially confined air space above the surface of the liquid material in reservoir 602. This confinement causes the air above the liquid to remain substantially saturated with the material. Hence, apertures 618 in lid 614 permit the escape of a substantially saturated mixture of air and material from reservoir 602. Replacement air seeps into reservoir 602 around the sides of lid 614.

When container 700 (or 900) is installed in cavity 309, protrusion 712 and adjacent shoulders 714 cooperate with housing front wall 302 to define an airway 730 (see FIGS. 1 through 5) which direct air forced through the housing by fan 404 downwardly and across reservoir 602. Because the top wall 720 of container 700 is raised above reservoir lid 614 by means of collar 724, sloped portion 722 cooperates with the lid to define an air passage 732 of decreasing cross-section for air flowing across the reservoir. The velocity of the air flow in the vicinity of reservoir 602 is therefore increased, with a corresponding reduction in static pressure. This reduced pressure enhances the removal of saturated air from reservoir 614, and the evaporation of material from the surface of the liquid in the reservoir into the air space thereabove. As the forced air flow passes across apertured reservoir lid 614, the air saturated with vaporized material is entrained therein and is exhausted to the ambient through channel 622 and outlet 307. If the rate of evaporation is insufficient, an absorbent wick (not shown) may be partially immersed in the material in reservoir 602 and extend outwardly therefrom into the air passage 732.

Material supply container 700 will automatically replenish material evaporated from reservoir 602 when the material level drops below the open mouth of outlet tube 726. This will break the vacuum created in supply container 700 and permit air to enter the container and displace a dispensed quantity of fresh liquid material. The material level within reservoir 602 will be brought back up to the level of the open mouth of outlet tube 726, at which time a liquid seal is again effected to discontinue the flow of material out of container 700. The fresh material is dispensed from supply container 700 directly onto the surface of the liquid in reservoir 602. Hence, the surface is continually renewed as the material evaporates, thereby preventing stagnation and encrustation of the surface, and insuring that the rate of evaporation remains substantially uniform. Because supply container 700 is air-tight, a supply of fresh material for replenishment is insured.

Although the present invention has been illustrated in terms of a preferred embodiment, it will be obvious to one of ordinary skill in the art that numerous modifications may be made without departing from the true spirit and scope of the invention which is to be limited only by the appended claims. For example, although a liquid air freshening material has been disclosed, it is clear that the dispenser of the invention can be used to dispense any vaporizable fluent substance, including liquid, powder and granular fluent substances. Furthermore, while a battery-powered dispenser has been described, it is envisioned that the dispenser could be powered by line current either directly to a motor designed to operate at higher voltage, or through a transformer which may replace the battery in the battery tray.

I claim:

1. A method of emitting vaporized material into the ambient at a controlled, substantially uniform rate from a reservoir containing an exposed liquid quantity of said material, said reservoir having an apertured lid substantially confining the air space above said liquid to cause the air above said liquid to remain substantially saturated with said material, said quantity being replenished from a replaceable, air-tight supply container of fresh liquid material removably supported above and in close proximity to said reservoir, thereby forming a narrow gap between a portion of the body of said container and said lid, comprising the steps of:

producing and directing a continuous forced flow of ambient air through said gap close to but substantially not in contact with the surface of the liquid in the reservoir to draw out said substantially saturated air from beneath said lid, effect vaporization of said liquid from said surface and entrain the vaporized material in said forced air flow; and continually and automatically replenishing material evaporated from said reservoir by discharging liquid material directly onto the surface of the liquid in the reservoir from said container to renew said surface and prevent stagnation thereof.

2. A method according to claim 1 wherein said supply container has a downwardly directed outlet in sealed fluid communication with said liquid surface, and the step of replenishing said material comprises dispensing fresh liquid from said container onto said surface when the liquid seal between said container outlet and said surface is broken by a drop in the surface level due to depletion of the liquid in the reservoir by vaporization thereof.

* * * * *